(12) United States Patent
Seelhorst et al.

(10) Patent No.: US 9,814,673 B2
(45) Date of Patent: *Nov. 14, 2017

(54) INTRAOCULAR LENS COMPRISING PHARMACEUTICAL COMPOSITIONS AND METHODS FOR FABRICATING THEREOF

(71) Applicant: IMPRIMIS PHARMACEUTICALS, INC., San Diego, CA (US)

(72) Inventors: Gary Seelhorst, San Diego, CA (US); Thomas Harvey, Eau Claire, WI (US); Mark L. Baum, San Diego, CA (US)

(73) Assignee: Imprimis Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/066,731

(22) Filed: Mar. 10, 2016

(65) Prior Publication Data

US 2016/0193144 A1 Jul. 7, 2016

Related U.S. Application Data

(63) Continuation-in-part of application No. 14/458,049, filed on Aug. 12, 2014.

(51) Int. Cl.
| | |
|---|---|
| A61K 9/00 | (2006.01) |
| A61K 31/4709 | (2006.01) |
| A61K 47/10 | (2017.01) |
| A61K 31/573 | (2006.01) |
| A61K 31/196 | (2006.01) |
| A61K 31/58 | (2006.01) |
| A61K 38/12 | (2006.01) |
| A61K 38/14 | (2006.01) |
| A61K 47/18 | (2017.01) |
| A61K 47/26 | (2006.01) |

(52) U.S. Cl.
CPC .......... *A61K 9/0051* (2013.01); *A61K 9/0019* (2013.01); *A61K 9/0048* (2013.01); *A61K 31/196* (2013.01); *A61K 31/4709* (2013.01); *A61K 31/573* (2013.01); *A61K 31/58* (2013.01); *A61K 38/14* (2013.01); *A61K 47/10* (2013.01); *A61K 47/183* (2013.01); *A61K 47/26* (2013.01)

(58) Field of Classification Search
CPC ....................................................... A61K 9/00
See application file for complete search history.

(56) References Cited

U.S. PATENT DOCUMENTS

| | | | | |
|---|---|---|---|---|
| 5,773,019 A * | 6/1998 | Ashton | ................. | A61F 9/0017 424/423 |
| 9,248,101 B2 * | 2/2016 | Moschwitzer | ....... | A61K 9/1694 |
| 2004/0198829 A1 * | 10/2004 | Sponsel | ............... | A61K 9/0048 514/573 |
| 2007/0049552 A1 * | 3/2007 | Babu | .................... | A61K 9/0014 514/58 |
| 2007/0298073 A1 | 12/2007 | Whitcup et al. | | |
| 2008/0221585 A1 * | 9/2008 | Downer | ............... | A61F 2/1678 606/107 |
| 2008/0262415 A1 | 10/2008 | Peyman | | |
| 2009/0130176 A1 | 5/2009 | Bossy-Nobs et al. | | |
| 2010/0239637 A1 * | 9/2010 | Ciolino | ................. | A61F 9/0017 424/429 |
| 2013/0178801 A1 * | 7/2013 | Branch | ................... | A61F 11/00 604/173 |
| 2014/0127269 A1 * | 5/2014 | Masli | ................... | A61K 9/0051 424/400 |
| 2016/0045432 A1 | 2/2016 | Seelhorst et al. | | |

FOREIGN PATENT DOCUMENTS

| | | | |
|---|---|---|---|
| WO | WO2008144347 | * | 5/2008 |
| WO | (WO2008/144347 | * | 11/2008 |
| WO | 2016/024956 A1 | | 2/2016 |

OTHER PUBLICATIONS

Sharma et al. (Moxifloxacin Loaded Contact Lens for Ocular Delivery—An In Vitro Study).Jan. 2011.*
Scripture et al. "The Last Hurdle—Taking Cataract Surgery Dropless," Cataract & Refractive Surgery Today, Jun. 2014, pp. 52-53, Bryn Mawr Communications LLC, Wayne, PA, USA.
Da Cunha et al. "Efficacy and Tolerability of a Gatifloxacin/Prednisolone Acetate Fixed Combination for Topical Prophylaxis and Control of Inflammation in Phacoemulsification: a 20-Day-Double-Blind Comparison to its Individual Components," Clinics, Jun. 2013, 68(6)834-839, FMUSP, Sao Paulo, Brazil.
Paganelli et al. "A Single Intraoperative Sub-Tenon's Capsule Injection of Triamcinolone and Ciprofloxacin in a Controlled-Release System for Cataract Surgery," Investigative Ophthalmology & Visual Science—IOVS, Association for Research in Vision and Ophthalmology, US, Jul. 2009, 50(7)3041-3047, ARVO Journals, Rockville, MD, USA.
Cardillo et al. "Subconjunctival Delivery of Antibiotics in a Controlled-Release System: A Novel Anti-Infective Prophylaxis Approach for Cataract Surgery," Archives of Ophthalmology, Jan. 2010, 128(1)81-87, AMA Publishing Group, Chicago, IL, USA.
Espiritu et al. "Efficacy and Tolerability of a Combined Moxifloxacin/Dexamethasone Formulation for Topical Prophylaxis in Phacoemulsification: An Open-Label Single-Arm Clinical Trial," Journal of Ophthalmology, 2011, vol. 2011, 5 pgs, Hindawi Publishing Corporation, New York, NY, USA.
Lipnitzki et al. "Hydrophilic Acrylic Intraocular Lens as a Drug Delivery System: Influence of the Presoaking Time and Comparison to Intracameral Injection," Journal of Ocular Pharmacology and Therapeutics, 2013, 29(4)414-418, Mary Ann Liebert, Inc. Publishers, New Rochelle, NY, USA.

(Continued)

*Primary Examiner* — David J Blanchard
*Assistant Examiner* — Sarah Alawadi
(74) *Attorney, Agent, or Firm* — Wagenknecht IP Law Group PC

(57) ABSTRACT

Medical articles are described, comprising a lens and a pharmaceutical composition incorporated into the lens, the compositions consisting essentially of a therapeutically effective quantity of an anti-bacterial agent (such as moxifloxacin), a therapeutically effective quantity of an anti-inflammatory agent (such as prednisolone) and at least one pharmaceutically acceptable excipient. Methods for fabricating the medical articles and using them are also described.

17 Claims, No Drawings

(56) References Cited

OTHER PUBLICATIONS

Gonzalez-Chomon et al. "Drug-Eluting Intraocular Lenses," Materials, Nov. 2011, 4(11)1927-1940, MDPI AG, Basel, Switzerland.
PCT/US2014/050751 International Search Report and Written Opinion dated Nov. 13, 2014.
Portoles et al. "Poloxamer 407 as a Bacterial Abhesive for Hydrogel Contact Lenses," Journal of Biomedical Materials Research, 1994, 28:303-309, John Wiley & Sons, Inc.

* cited by examiner

INTRAOCULAR LENS COMPRISING PHARMACEUTICAL COMPOSITIONS AND METHODS FOR FABRICATING THEREOF

CROSS REFERENCE TO RELATED APPLICATION

This is a continuation-in-part patent application of U.S. patent application Ser. No. 14/458,049 filed on Aug. 12, 2014, entitled "Intraocular Lens Comprising Pharmaceutical Compositions and Methods for Fabricating Thereof," and claims priority under 35 U.S.C. §120 to the same, the entire contents of which is hereby incorporated by reference.

FIELD OF THE INVENTION

The present invention relates generally to the field of ophthalmology and more specifically to injectable ophthalmological compositions having anti-bacterial and anti-inflammatory properties, and to methods of preparing such compositions.

BACKGROUND

In ophthalmological treatments and procedures, e.g., cataract surgery, pre- and post-operative eye drops are frequently used by the patients to eliminate or alleviate negative post-surgery complications such as infections, inflammation, and tissue edema. It has been reported that as many as 8% of all ocular surgery patients may suffer from infections, including the potentially catastrophic endophthalmitis, and various negative sight threatening side effects after surgery, such as inflammatory uveitis, corneal edema, and cystoid macular edema. Typically, the topical postoperative medications are prescribed for at-home use starting before and then after cataract surgery, and are typically self-administered, unless requiring a caregiver or family assistance.

These ophthalmic medication drops include anti-inflammatory and antibiotic agents and are highly effective, but require strict adherence to the treatment regimens, which is often difficult for many patients (with physical limitations or aversions to eyelid touching and manipulation) and is frequently expensive (well over $200 per procedure), causing patients' dissatisfaction. It is desirable to have an alternative procedure that would permit avoiding the necessity of the use of such post-surgery medications to save the associated post-operative trouble and expenses.

One such alternative procedure includes the intraoperative intravitreal injection by an atraumatic transzonular route that can achieve patient outcomes that are as good as, or better than, the current at-home eye drop regimen, removing the issues of compliance and medication administration accuracy. This patent specification discloses pharmaceutical compositions suitable for intraoperative ocular injections that can achieve such positive patient outcomes, and methods of fabricating and administering the same.

SUMMARY

According to one embodiment of the invention, a pharmaceutical composition for intraocular injection is provided, the composition comprising a therapeutic component consisting essentially of a therapeutically effective quantity of an anti-bacterial agent and a therapeutically effective quantity of an anti-inflammatory agent, and at least one pharmaceutically acceptable excipient and/or a pharmaceutically acceptable carrier that are suitable for intraocular injection.

According to another embodiment of the invention, an anti-bacterial agent described herein can be a compound selected from the group of quinolone (including a fluorinated quinolone), e.g., moxifloxacin, and pharmaceutically acceptable salts, hydrates, solvates or N-oxides thereof.

According to yet another embodiment of the invention, an anti-inflammatory agent described herein can be a corticosteroid, e.g., triamcinolone, and pharmaceutically acceptable salts, hydrates, solvates, ethers, esters, acetals and ketals thereof According to other embodiments of the invention, the pharmaceutical compositions described herein may be formulated as two-phase suspensions incorporated into a lens, suspensions consisting of a dispersed phase consisting of solid particles of corticosteroid(s) and a dispersion medium in which the dispersed phase is dispersed, the dispersion medium consisting of anti-bacterial agent(s) (e.g., various quinolone(s)), solubilizing and suspending agent(s), such as non-ionic polyoxyethylene-polyoxypropylene block copolymer(s), optionally, a therapeutically effective quantity of glycopeptide antibiotic(s), optionally, a therapeutically effective quantity of non-steroid anti-inflammatory drug(s), and a pharmaceutically acceptable carrier.

According to other embodiments of the invention, the pharmaceutical compositions described herein may be intravitreally transzonularly injected into a mammalian subject as a part of the process of treatment of a variety of ophthalmological diseases, conditions or pathologies associated with intraocular surgery, such as cataracts, retinal and glaucoma disease.

DETAILED DESCRIPTION

A. Terms and Definitions

Unless specific definitions are provided, the nomenclatures utilized in connection with, and the laboratory procedures and techniques of analytical chemistry, synthetic organic and inorganic chemistry described herein, are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, formulating compositions and testing them. The foregoing techniques and procedures can be generally performed according to conventional methods well known in the art.

It is to be understood that both the foregoing general description and the following detailed description are exemplary and explanatory only and are not restrictive of the invention claimed. As used herein, the use of the singular includes the plural unless specifically stated otherwise. The section headings used herein are for organizational purposes only and are not to be construed as limiting the subject matter described.

As used herein, "or" means "and/or" unless stated otherwise. Furthermore, use of the term "including" as well as other forms, such as "includes," and "included," is not limiting.

"About" as used herein means that a number referred to as "about" comprises the recited number plus or minus 1-10% of that recited number. For example, "about" 100 degrees can mean 95-105 degrees or as few as 99-101 degrees depending on the context. Whenever it appears herein, a numerical range such as "1 to 20" refers to each integer in the given range; i.e., meaning only 1, only 2, only 3, etc., up to and including only 20.

The term "pharmaceutical composition" is defined as a chemical or a biological compound or substance, or a mixture or combination of two or more such compounds or substances, intended for use in the medical diagnosis, cure, treatment, or prevention of disease or pathology.

The term "suspension" is defined for the purposes of the present application as a two-phase dispersion system having a first phase and a second phase. It is further specifically provided that dispersion systems having three, four or more phases are not within the meaning of "suspension" for the purposes of the instant application.

Furthermore, the above mentioned first phase of the suspension consists of a multitude of solid particles and is designated and defined as the "dispersed phase", and the above mentioned second phase of the suspension is a liquid and is designated and defined as the "dispersion medium", or, interchangeably and synonymously, the "continuous phase".

Furthermore, the above mentioned "dispersed phase" is dispersed in the above mentioned "dispersion medium", and the term "dispersed" is defined as meaning that the "dispersed phase" is statistically evenly distributed throughout the entire volume of the suspension, with no statistically meaningful deviations in the concentrations of the dispersed phase in different portions of the suspension.

The term "intraocular injection" refers to an injection that is administered by entering the eyeball of the patient.

The term "transzonular" refers to an injection administered through the ciliary zonule which is a series of fibers connecting the ciliary body and lens of the eye.

The term "intravitreal" refers to an injection administered through an eye of the patient, directly into the inner cavity of the eye.

The term "intraoperative" is defined as an action occurring or carried during, or in the course of, surgery.

The term "intraocular lens" or "IOL" is defined as lens implanted in the eye used to treat cataracts or myopia, and as used herein, the IOL is inclusive of both phakic and pseudophakic IOL and is also inclusive of the IOL fabricated from both hydrophilic and hydrophobic materials as the terms "hydrophilic" and "hydrophobic" are understood by those having ordinary skill in the art.

The terms "incorporated" and "ensconced" are used herein to mean combining two or more separate elements as to form an indistinguishable whole that cannot be easily separated into the original constituent part. For instance, when the instant application recites "incorporating" or "ensconcing" a pharmaceutical composition into the IOL, it means that once the pharmaceutical composition is so ensconced, it cannot be physically separated from the IOL, in a reasonably easy fashion.

The terms "anti-bacterial" and "antibiotic" used herein interchangeably, refer to substances or compounds that destroy bacteria and/or inhibit the growth thereof via any mechanism or route.

The term "anti-inflammatory" refers to substances or compounds that counteract or suppress inflammation via any mechanism or route.

The terms "non-steroid anti-inflammatory drug" or "NSAID" refer to substances or compounds that are free of steroid moieties and provide analgesic, antipyretic and/or anti-inflammatory effects.

The term "quinolone" for the purposes of this application refers to a genus of anti-bacterial compounds that are derivatives of benzopyridine and in some embodiments include fluorine atom, such as in the following structure ("fluoroquinolone"):

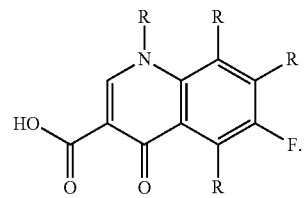

The terms "corticosteroid" and closely related "glucocorticoid" are defined as compounds belonging to a sub-genus of steroids that are derivatives of corticosterone, the latter having the chemical structure:

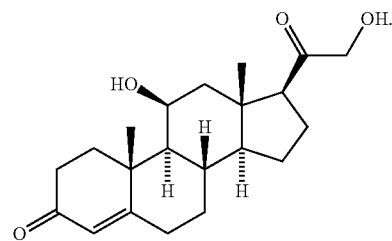

The term "salt" refers to an ionic compound which is a product of the neutralization reaction of an acid and a base.

The terms "solvate" and "hydrate" are used herein to indicate that a compound or a substance is physically or chemically associated with a solvent for "solvates" such as water (for "hydrates").

The term "ether" refers to a chemical compound containing the structure R—O—$R_1$, where two organic fragments R and $R_1$ are connected via oxygen.

The term "ester" refers to a chemical compound containing the ester group R—O—C(O)—$R_1$, connecting two organic fragments R and $R_1$.

The terms "acetal" and "ketal" refer to a chemical compound containing the functional group R—C($R_1$)(OR$_2$)$_2$, where R and $R_2$ are organic fragments and $R_1$ is hydrogen atom (for acetals), and is inclusive of "hemiacetals" where one $R_2$ (but not the other) is hydrogen atom; or where none of R, $R_1$ and $R_2$ is a hydrogen atom and each is an organic fragment (for ketals).

The term "carrier" refers to a substance that serves as a vehicle for improving the efficiency of delivery and the effectiveness of a pharmaceutical composition.

The term "excipient" refers to a pharmacologically inactive substance that is formulated in combination with the pharmacologically active ingredient of pharmaceutical composition and is inclusive of bulking agents, fillers, diluents and products used for facilitating drug absorption or solubility or for other pharmacokinetic considerations.

The term "therapeutically effective amount" is defined as the amount of the compound or pharmaceutical composition that will elicit the biological or medical response of a tissue, system, animal or human that is being sought by the researcher, medical doctor or other clinician.

The term "pharmaceutically acceptable" is defined as a carrier, whether diluent or excipient, that is compatible with the other ingredients of the formulation and not deleterious to the recipient thereof.

The terms "administration of a composition" or "administering a composition" is defined to include an act of providing a compound of the invention or pharmaceutical composition to the subject in need of treatment.

B. Embodiments of the Invention

According to embodiments of the present invention, pharmaceutical compositions intended to prevent and/or treat inflammation and/or infections are provided. The compositions include an active component comprising, consisting essentially of, or consisting of a therapeutically effective quantity of an anti-bacterial agent (i.e., an antibiotic) and a therapeutically effective quantity of an anti-inflammatory agent (e.g., a corticosteroid). In some embodiments, the pharmaceutical compositions can be used for intraocular injections. In other embodiments the pharmaceutical compositions can be used for intra-articular or intra-lesional use. The compositions further include one or several pharmaceutically acceptable excipient(s) and one or several pharmaceutically acceptable carrier(s).

The concentration of the anti-bacterial agent in the pharmaceutical composition may be between about 0.01 mg/mL and about 50.0 mg/mL, such as between about 0.5 mg/mL and about 10 mg/mL, for example, about 1.0 mg/mL. The concentration of the anti-inflammatory agent in the pharmaceutical composition may be between about 0.1 mg/mL and about 100.0 mg/mL, such as between about 5.0 mg/mL and about 50.0 mg/mL, for example, about 15.0 mg/mL.

According to further embodiments, the anti-bacterial agent to be employed in the active component of the composition may be selected from the group of quinolones, including fluoroquinolones, and suitable derivatives of the same, such as pharmaceutically acceptable salts, hydrates or solvates thereof. In one embodiment, fluoroquinolone that may be so employed is moxifloxacin (chemically, 1-cyclopropyl-7-[(1S,6S)-2,8-diazabicyclo-[4.3.0]non-8-yl]-6-fluoro-8-methoxy-4-oxo-quinoline-3-carboxylic acid), which is available, e.g., under trade name Avelox® from Bayer Healthcare Corp. of Wayne, N.J., and under other trade names from other suppliers such as Alcon Corp. and Bristol-Myers Squibb Co. and has the following chemical structure:

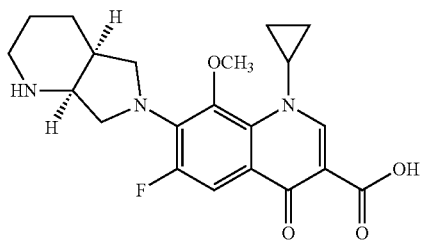 [SMILES: COc1c(N2C[C@@H]3CCCN[C@@H]3C2)c(F)cc2c(=O)c(C(=O)O)cn(C3CC3)c12]

A non-limiting example of a possible alternative fluoroquinolone antibiotic that may be used instead of, or in combination with, moxifloxacin is gatifloxacin. In some embodiments one or several glycopeptide antibiotic(s), or a combination of some or all of them, may be optionally used as a part of the anti-bacterial agent, in combination with moxifloxacin. One example of such an acceptable additional glycopeptide antibiotic is vancomycin which can be introduced into the pharmaceutical composition at a concentration between about 1 mg/mL and about 100.0 mg/mL, such as between about 5.0 mg/mL and about 50.0 mg/mL, for example, about 10.0 mg/mL. Vancomycin is available under the trade name Vancocin® from Eli Lilly & Co. of Indianapolis, Ind. Other acceptable additional glycopeptide antibiotics that may be used include teicoplanin, televancin, decaplanin, ramoplanin, gentamicin, tobramycin, amikacin, cefuroxime, polymyxin B sulfate, and trimethoprim.

According to further embodiments, the anti-inflammatory agent to be employed in the active component of the composition may be selected from the group of corticosteroids, such as derivatives of corticosterone, and pharmaceutically acceptable salts, hydrates, solvates, ethers, esters, acetals and ketals thereof. For example, a product obtained as a result of a chemically reasonable substitution of any hydrogen and/or hydroxyl group in the molecule of corticosterone may be used. In one embodiment, a corticosteroid that can be so utilized is triamcinolone (chemically, (11β,16α)-9-fluoro-11,16,17,21-tetrahydroxypregna-1,4-diene-3,20-dione) having the following chemical formula:

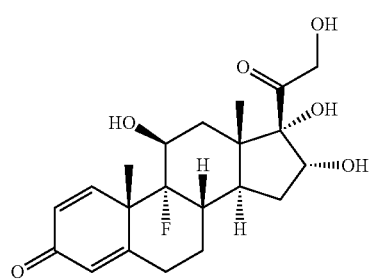

In another embodiment, a corticosteroid that can be so utilized is triamcinolone acetonide (chemically, (4aS,4bR,5S,6aS,6bS,9aR,10aS,10bS)-4b-fluoro-6b-glycoloyl-5-hydroxy-4a,6a,8,8-tetramethyl-4a,4b,5,6,6a,6b,9a,10,10a,10b,11,12-dodecahydro-2H-naphtho[2',1':4,5]indeno[1,2-d][1,3]dioxol-2-one) which is a ketal derivative of triamcinolone available, e.g., under the trade name Kenalog® from Bristol-Myers Squibb Co. of Princeton, N.J., and under other trade names from other suppliers, and having the following chemical formula:

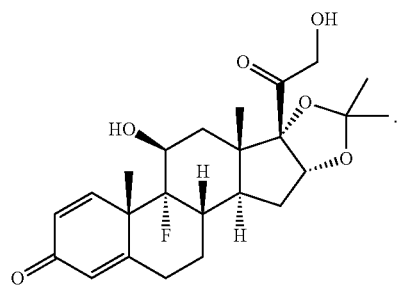

Other corticosteroids, or a combination of some or all of them, may be used instead of all or a portion of triamcinolone and/or of all or a portion of triamcinolone acetonide. Some non-limiting examples of such acceptable other corticosteroids or glucocorticoids include triamcinolone diacetate, triamcinolone benetonide, triamcinolone furetonide, triamcinolone hexacetonide, betamethasone acetate, dexamethasone, fluorometholone and fluocinolone acetonide, prednisone, prednisolone, methylprednisone, corticol, cortisone, fluorocortisone, deoxycorticosterone acetate, aldosterone, budesonide and derivatives, analogs or combinations thereof.

According to other embodiments, pharmaceutical compositions described herein may further optionally include pharmaceutically effective quantities of one or several non-steroid anti-inflammatory drug(s) or NSAID(s). The concentration of NSAID(s) in the pharmaceutical composition, if used, may be between about 0.1 mg/mL and about 100.0 mg/mL, such as between about 5.0 mg/mL and about 50.0 mg/mL, for example, about 15.0 mg/mL.

If the pharmaceutical compositions disclosed herein do include NSAID(s), it is envisioned that some compositions should be free of the specific NSAID, bromfenac. In other embodiments, however, bromfenac may be used as well as such NSAID(s) as any of ketorolac, etodolac, sulindac, diclofenac, aceclofenac, nepafenac, tolmetin, indomethacin, nabumetone, ketoprofen, dexketoprofen, ibuprofen, flurbiprofen, dexibuprofen, fenoprofen, loxoprofen, oxaprozin, naproxen, aspirin, salicylic acid, diflunisal, salsalate, mefenamic acid, meclofenamic acid, flufenamic acid, tolfenamic acid, meloxicam, piroxicam, ternoxicam, droxicam, lornoxicam, isoxicam, celecoxib, rofecoxib, valdecoxib, parecoxib, lumiracoxib, etoricoxib, firocoxib, nimesulide, clonixin, licofelone, and pharmaceutically acceptable salts, hydrates, solvates, ethers, esters, acetals and ketals thereof As mentioned above, the pharmaceutical composition that is the subject matter of the instant application may further optionally include one or several pharmaceutically acceptable excipient(s). Those having ordinary skill in the art will be able to select the suitable excipient(s). It is worth mentioning that when moxifloxacin is used in pharmaceutical formulations, it is often difficult to obtain a stable suspension of another product (e.g., a corticosteroid such as triamcinolone acetonide) that is present in the same formulation and that needs to be in a form of a stable suspension. Without being bound by any particular scientific theory, such difficulties in obtaining the stable suspension are believed to be caused by moxifloxacin's tendency to deactivate many suspending agents resulting in unacceptable coagulation, clumping and flocculation. As a result, normal delivery through a typical 27-29 gauge cannula is often difficult or even impossible.

Therefore, it is desirable to select an excipient that is stable in the presence of moxifloxacin and can, therefore, be used as a solubilizing and suspending agent to ensure that the corticosteroid such as triamcinolone acetonide safely forms a stable suspension even when moxifloxacin is also present in the same formulation. Numerous attempts by others to produce a stable moxifloxacin/triamcinolone acetonide pharmaceutical composition suitable for intraocular injection have not been successful.

In some embodiments, an excipient that can be used as a solubilizing and stabilizing agent to overcome the above-described difficulties and thus to obtain a stable suspension of the corticosteroid such as triamcinolone acetonide may be a non-ionic polyoxyethylene-polyoxypropylene block copolymer having the following general structure:

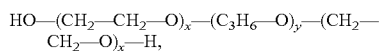

wherein x is an integer having the value of at least 8 and x is an integer having the value of at least 38.

If a non-ionic polyoxyethylene-polyoxypropylene block copolymer is used as a solubilizing and stabilizing agent in the pharmaceutical compositions of the instant invention, its contents in the overall composition may be between about 0.01 mass % and about 10.0 mass % such as between about 1.0 mass % and about 8 mass %, for example, about 5.0 mass %.

One non-limiting example of a specific non-ionic polyoxyethylene-polyoxypropylene block copolymer that can be used as a solubilizing and stabilizing agent in the pharmaceutical compositions of the instant invention is the product known under the trade name Poloxamer 407® (poly(ethylene glycol)-block-poly(propylene glycol)-block-poly(ethylene glycol)) available from Sigma-Aldrich Corp. of St. Louis, Mo., with the molecular weight of the polyoxypropylene portion of about 4,000 Daltons, about a 70% polyoxyethylene content, the overall molecular weight of between about 9,840 Daltons and about 14,600 Daltons and having the following chemical structure:

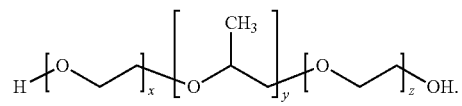

Non-limiting examples of some other excipients and carriers that may be used in preparing in the pharmaceutical compositions of the instant invention include polysorbate (an emulsifier), edetate calcium disodium (EDTA, a chelating agent), hydrochloric acid (the pH adjuster) and sterile water.

According to further embodiments, methods for fabricating the above-described pharmaceutical compositions are provided. A one-batch formulation method may be used, where the components of the pharmaceutical formulation can be combined in single container; the components may be added to the container simultaneously or consecutively.

In one exemplary, non-limiting procedure, a quantity of an anti-bacterial agent such as moxifloxacin may be placed into a mixing container followed by adding a quantity of sterile water and hydrochloric acid to obtain a slightly acidic mixture (e.g., having pH of about 6.5) which is stirred until a clear solution is obtained. In case of moxifloxacin/HCl system, the solution is stable, allowing the formulation to remain closed system thus preventing contamination and the loss of sterility.

Next, a quantity of corticosteroid such as micronized triamcinolone acetonide, a quantity of Poloxamer 407®, a quantity of edetate calcium disodium and a quantity of polysorbate 80 may be all added to be combined in the same container with the already prepared moxifloxacin/HCl solution and stirred together (e.g., by spinning) for a period of time, e.g., about 6 hours, until a homogenous suspension has been obtained. The resulting suspension may then be transferred into single dose vials, capped, sealed, autoclaved and shaken until cool. Finally, a complete testing for sterility and the presence of endotoxin may be performed on the product according to commonly used methods known to those having ordinary skill in the art.

From the description above, it, therefore, follows that according to embodiments of the present application, the pharmaceutical compositions described herein can be formulated as stable two-phase suspensions as defined above. More specifically, according to these embodiments, the suspensions at issue consist of two phases, i.e., the dispersed phase that is dispersed within the dispersion medium. The dispersed phase consists of solid particles consisting of a therapeutically effective quantity of a corticosteroid. No compounds other that corticosteroids described hereinabove are present within the solid particles that form the dispersed phase.

According to such embodiments, the dispersion medium is a liquid that includes all other compounds that are present in the pharmaceutical compositions described in the application. The application envisions no embodiment where corticosteroid can be used outside the dispersed phase such as in the dispersion medium. Specifically, the dispersion medium includes the following components (a)-(e):

(a) at least one anti-bacterial agent of the quinolone group (i.e., quinolone, a fluorinated quinolone and derivatives as described);

(b) at least one solubilizing and suspending agent (i.e., non-ionic polyoxyethlene-polyoxypropylene block copolymers or polysorbates);

(c) at least one glycopeptide antibiotic (i.e., vancomycin, or other antibiotic(s) described hereinabove), the use of this component in the dispersion medium is optional;

(d) also optionally, at least one non-steroid anti-inflammatory drug such as bromfenac or other NSAIDs described hereinabove; and (e) a carrier.

In one exemplary, non-limiting procedure, the process of preparing the pharmaceutical compositions described hereinabove may commence by forming the aqueous dispersion medium. To form the aqueous dispersion medium, a quantity of an anti-bacterial agent such as moxifloxacin may be put into a mixing container followed by adding a quantity of sterile water and hydrochloric acid to obtain a slightly acidic mixture (e.g., having a pH of about 6.5) which can be stirred until a clear solution is obtained. In case of moxifloxacin/HCl system, the solution is stable, allowing the formulation to remain closed system thus preventing contamination and the loss of sterility.

After such clear stable solution has been formed, more components could be added to the solution that is to become the dispersion medium of the final suspension, i.e., a quantity of Poloxamer 407® and/or a quantity of polysorbate 80, a quantity of edetate calcium disodium, optionally a quantity of an antibiotic (e.g., vancomycin) and optionally a quantity of an NSAID (e.g., bromfenac) may be all added to the same container with the already prepared moxifloxacin/HCl solution.

At the same time, a quantity of corticosteroid such as micronized triamcinolone acetonide can be added to the above described solution, followed by stirring everything together (e.g., by spinning) for a period of time, e.g., about 6 hours, until a homogenous suspension has been obtained. In that suspension two phases can be formed: the dispersed phase of the corticosteroid and the dispersion medium into which the aqueous solution described above has now been transformed.

Pharmaceutical compositions prepared as described above can be used to prevent complications that may arise after ophthalmic surgical operations and procedure. For example, the formulations can be used during any intraocular surgery, such as cataract surgery, planned vitrectomy or glaucoma procedures, to prevent or at least substantially reduce the risk of post-surgery complications, such as the development of endophthalmitis or cystoid macular edema (CME), without having the patient use pre- or post-operative topical ophthalmic drops. Individuals with evidence of endophthalmitis from prior surgical procedures or traumatic ocular penetration will benefit from concurrent injection of these formulations to sterilize infection and reduce damaging inflammation.

Pharmaceutical formulations described herein can be delivered via intraocular intravitreal injection which can be transzonular, or, if desired not transzonular. Intraocular intravitreal injection of this formulation, whether done via transzonular or via direct pars plana (trans-scleral) injection, delivers potent broad spectrum antibiotics directly into the suppurative tissue without requiring the urgent compounding of multiple individual medications or multiple individual injections into the eye.

Typically, a pharmaceutical composition described above will be intraocularly administered to a mammalian subject (e.g., humans, cats, dogs, other pets, domestic, wild or farm animals) in need of emergent, urgent or planned ophthalmic surgery treatment. The effect achieved by such use of pharmaceutical composition described above may last up to four weeks. The composition is to be injected intravitreally and trans-zonularly using methods and techniques known to those having ordinary skilled in the art of ophthalmology. In some embodiments, the injection can be intraoperative.

Typically, the delivery through a typical 27 gauge cannula can be employed utilizing a 1 mL TB syringe, with attention to re-suspending the formulation using momentary flicks and shake just prior to injection. The medicinal volume (i.e., dosage) required of this formulation varies based on the type of intraocular procedure, the degree of postoperative inflammation induced or anticipated, the risk assessment for postoperative infection, and anatomic considerations regarding the available volume for the injection being added to a closed intraocular space.

It is worth mentioning that while intracameral (that is, anterior chamber) injections are within the scope of the instant invention such injections instead of posterior chamber (intravitreal) injection may not be satisfactory in some cases, as the suspension clogs the trabecular meshwork and aggravates intraocular drainage, resulting in an intraocular pressure rise postoperative. This is avoided with intravitreal injection, in addition to retaining the formulation components into the protein matrix of the vitreous of a greater duration. Anterior chamber wash out occurs over hours (antibiotic in solution) and days (steroid in suspension), while intravitreal injection is retained for weeks.

In alternative embodiments, if desired or necessary the formulations may also be delivered in the form of eye drops or eye sprays, as well as via subconjunctival injection, intraocular intracameral injection, sub-tenon injection, intra-articular injection or intra-lesional injection, particularly, in, but not limited to, some cases when necessary to deliver additional medication when local ocular inflammation and extra-ocular infection need suppression. Intravitreal delivery of steroid has historically been used to treat clinically significant cystoid macular edema (CME); the application of this formulation into the vitreous during routine intraocular procedures brings more aggressive prophylaxis against CME occurrence. Additionally, the suspension of this formulation is useful for staining vitreous during planned and unplanned vitrectomies, improving visualization of this otherwise transparent intraocular tissue, improving vitrectomy outcomes and reducing complications resulting from inadequate or tractional vitreous removal. In still further embodiments, there is also envisioned intra-canalicular delivery, i.e., delivery via a lacrimal canaliculus implant.

In some further alternative embodiments, instead of delivering the above-described compositions comprising both anti-bacterial and anti-inflammatory agents, consecutive injections may be used instead, if desired. For example, triamcinolone or prednisolone may be injected first, immediately followed by the injection of moxifloxacin or vice versa.

In still further embodiments, the pharmaceutical compositions described hereinabove may be incorporated into a lens, such as an intraocular lens or a contact lens. The lens can be made of a hydrophobic or a hydrophilic material, as desired. One non-limiting example of such a material may be poly(2-hydroxyethyl methacrylate) (HEMA). The lens made of other materials may be also selected by those having ordinary skill in the art. The pharmaceutical compositions may be incorporated into a lens, such as an intraocular lens before the IOL is implanted in a surgical procedure such as a cataract surgery or a surgery that is performed to correct myopia. To illustrate, a pharmaceutical composition to be used for these purposes may include any corticosteroid and any anti-bacterial agent described above, to be selected by a skilled practitioner.

To further exemplify but not to unduly limit, a composition to be incorporated into the lens such as the IOL may include a corticosteroid such as triamcinolone, prednisone, prednisolone or dexamethasone and an anti-bacterial agent, e.g., moxifloxacin or gatifloxacin. Further components of a pharmaceutical composition to be incorporated into the IOL optionally include solubilizing and suspending agent such as Poloxamer 407® and also optionally an additional antibiotic such as vancomycin, as described above.

To incorporate a pharmaceutical composition into the IOL, a variety of methods may be employed. In one exemplary non-limiting embodiment, the IOL may be immersed, under ambient conditions, into a solution of a selected pharmaceutical composition that is to be incorporated into the IOL. Without being bound by any particular scientific theory, it appears the process of incorporation can occur by adsorption. The time necessary to have the IOL adsorb the required quantity of the solution may be between about 6 hrs and 48 hours, for example, between about 12 hrs and about 36 hrs, such as about 24 hrs, followed by optional additional immersion of the IOL (now having the pharmaceutical composition ensconced into the IOL) into a saline solution for additional period of time of about 24 hrs, if desired.

It will be understood by those having ordinary skill in the art that the specific dose level and frequency of dosage for any particular patient may be varied and will depend upon a variety of factors including the activity of the specific compound employed, the metabolic stability and length of action of that compound, the age, body weight, general health, gender, diet, and the severity of the particular ophthalmological condition being treated.

In additional embodiments, pharmaceutical kits are provided. The kit includes a sealed container approved for the storage of pharmaceutical compositions, the container containing one of the above-described pharmaceutical compositions. An instruction for the use of the composition and the information about the composition are to be included in the kit.

The following examples are provided to further elucidate the advantages and features of the present invention, but are not intended to limit the scope of the invention. The examples are for the illustrative purposes only. USP pharmaceutical grade products were used in preparing the formulations described below.

C. Examples

EXAMPLE 1

Preparing a Pharmaceutical Composition

A pharmaceutical composition was prepared as described below. The following products were used in the amounts and concentrations specified:

(a) about 1.5 g of triamcinolone acetonide, at a concentration of about 15.0 mg/mL;

(b) about 0.1 g of moxifloxacin hydrochloride, at a concentration of about 1.0 mg/mL;

(c) about 1 mL of polysorbate 80, at a concentration of about 1.0 mass %;

(d) about 0.2 g of edetate calcium disodium, at a concentration of about 0.2 mass %;

(e) about 1 g of Poloxamer 407®, at a concentration of about 1.0 mass %;

(f) hydrochloric acid, to adjust pH to about 6.5; and (g) about 100.0 mL of sterile water for injection.

Moxifloxacin hydrochloride was placed into a de-pyrogenated beaker with a spin bar. Sterile water for injection was added to about ⅓ of the volume of the beaker. While spinning, moxifloxacin was dissolved by adding hydrochloric acid until a clear solution having the final pH of about 6.5 was obtained.

The solution was combined with micronized triamcinolone acetonide, Poloxamer 407®, edetate calcium disodium and polysorbate 80 and allowed to spin for about 6 hours until a hydrated and homogenous suspension was obtained.

The suspension was transferred into de-pyrogenated, single dose vials (2 mL size), capped and sealed, followed by autoclaving and shaking the vials until cool. Complete sterility and endotoxin testing was performed by an outside laboratory to ensure safety.

The formulation prepared as described above was tested for the particle sizes and their distribution. The results showed that very fine particles were obtained and the size distribution was quite uniform. Specifically, about 99% of all the particles had the diameter of 5 µM or less, where the sizes within the range between about 1 µM and 4 µM dominated and constituted about 82% of all particles. Just 0.1 to 0.2% of all the particles were large than about 10 µM in diameter.

The formulation prepared as described above was also tested for stability after 6 months of storage. After this period of storage no loss of potency was observed (as measured by HPLC); the formulation was visually stable at room temperature and readily re-suspended with gentle shaking with no increase of particle size or flocculation.

EXAMPLE 2

Preparing a Pharmaceutical Composition Containing Vancomycin

A pharmaceutical composition was prepared as described in Example 1, supra. The composition was autoclaved and sonicated for about 60 minutes and about 96 mL of the composition were combined with about 4 mL of vancomycin at a concentration of about 250 mg/mL. The pH of the mixture was adjusted to about 6.0-6.5 using hydrochloric acid. The product was then transferred into vials (at about 1 mL plus 5 drops per vial) and frozen. The product has kept its stability and potency for at least six months.

EXAMPLE 3

Using a Pharmaceutical Composition

A pharmaceutical composition fabricated as described in Example 1, supra, was administered to about 1,600 patients. To each, it was introduced using intravitreal transzonular injection. The injection was intraoperative. Only a very few patients, at the rate of about only 1 in 4,000, have developed any infection or suffered from other side effects that required further treatment, which is a substantial improvement over a typical rate of about 8% for the patients that did not receive the injection.

EXAMPLE 4

Incorporating a Pharmaceutical Composition into an IOL

A pharmaceutical composition was prepared as described in Example 2, supra. An IOL made of HEMA having about 26% water content was immersed into the composition for about 24 hours. The lens was a posterior chamber mono focal IOL known in the industry as SOFTEC HD.

After the 24 hr long immersion in the pharmaceutical composition, the lens was than immersed into a standard saline solution for additional 24 hours resulting in clear lens that was ready for installation.

EXAMPLE 5

Preparing a Pharmaceutical Composition Containing NSAID Bromfenac

A pharmaceutical composition was prepared as described below. The following products were used in the amounts specified:

(a) about 10.0 g of micronized prednisolone acetate;
(b) about 5.454 g of moxifloxacin hydrochloride monohydrate;
(c) about 1.035 g of bromfenac sodium powder;
(d) about 10.0 mL of an aqueous solution of polysorbate 80, at a concentration of about 1.0 mass %;
(e) about 4.0 g of boric acid powder;
(f) about 14.0 g of Poloxamer 407®;
(g) about 3.17 g of sodium chloride granules;
(h) 20% solution of sodium hydroxide, to adjust pH; and
(i) about 1.0 L of sterile water for injection.

Moxifloxacin hydrochloride was placed into a de-pyrogenated beaker with a spin bar. Sterile water for injection was added, about 60% of the total volume of water. While spinning, moxifloxacin was dissolved by adding sodium hydroxide to adjust the pH to about 7.4 to 7.8, followed by additional stirring for about 5 minutes, until a clear solution was obtained. Bromfenac was then added, with continued stirring, until completely dissolved which is indicated by the solution being visibly clear. The pH then was adjusted again to maintain it in the range of 7.4 to 7.8.

The solution was combined with polysorbate 80, Poloxamer 407 and boric acid, with continued stirring, followed by slowly adding micronized prednisolone acetate, the remainder of water, with continued spinning for about 20 minutes, until a hydrated and homogenous product was obtained.

The product was then transferred into pre-sterilized de-pyrogenated, 100 mL vials, capped and sealed, followed by autoclaving (about 121° C. and about 15.0 psi of pressure for about 30 minutes) shaking and sonicating the vials for about 30 minutes.

The composition obtained as described in this Example can then be incorporated into an IOL as described in Example 4, supra.

Although the invention has been described with reference to the above examples, it will be understood that modifications and variations are encompassed within the spirit and scope of the invention. Accordingly, the invention is limited only by the following claims.

What is claimed is:

1. A medical article of manufacture, consisting of:
   (a) an intraocular lens that is originally free of pharmaceutically active compounds; and
   (b) a pharmaceutical composition incorporated into the lens, wherein the pharmaceutical composition is a suspension consisting of:
      (b 1) a dispersed phase consisting of solid particles consisting of a therapeutically effective quantity of a corticosteroid and pharmaceutically acceptable salts, hydrates, solvates, ethers, esters, acetals and ketals thereof; and
      (b2) a dispersion medium consisting of:
         (1) a therapeutically effective quantity of an anti-bacterial agent independently selected from the group consisting of quinolone, a fluorinated quinolone and pharmaceutically acceptable salts, hydrates, solvates or N-oxides thereof;
         (2) a therapeutically effective quantity of a pharmaceutically acceptable solubilizing and suspending agent selected from the group consisting of non-ionic polyoxyethlene-polyoxypropylene block copolymers and polysorbates;
         (3) a therapeutically effective quantity of a glycopeptide antibiotic selected from the group consisting of vancomycin, teicoplanin, telavancin, decaplanin, ramoplanin, gentamicin, tobramycin, amikacin, cefuroxime, polymyxin B sulfate, and trimethoprim;
         (4) a therapeutically effective quantity of a non-steroid anti-inflammatory drug selected from the group consisting of bromfenac, ketorolac, etodolac, sulindac, diclofenac, aceclofenac, nepafenac, tolmetin, indomethacin, nabumetone, ketoprofen, dexketoprofen, ibuprofen, flurbiprofen, dexibuprofen, fenoprofen, loxoprofen, oxaprozin, naproxen, aspirin, salicylic acid, diflunisal, salsalate, mefenamic acid, meclofenamic acid, flufenamic acid, tolfenamic acid, meloxicam, piroxicam, ternoxicam, droxicam, lornoxicam, isoxicam, celecoxib, rofecoxib, valdecoxib, parecoxib, lumiracoxib, etoricoxib, firocoxib, nimesulide, clonixin, licofelone, and pharmaceutically acceptable salts, hydrates, solvates, ethers, esters, acetals and ketals thereof; and
         (5) a pharmaceutically acceptable carrier,
   wherein the dispersed phase is dispersed within the dispersion medium, and wherein at least about 99.8% of all the solid particles in the dispersed phase have a size of 10 µM or less.

2. The medical article of claim 1, wherein the anti-bacterial agent is a fluorinated quinolone selected from the group consisting of moxifloxacin and gatifloxacin.

3. The medical article of claim 1, wherein the corticosteroid is selected from the group consisting of triamcinolone, triamcinolone acetonide, triamcinolone diacetate, triamcinolone benetonide, triamcinolone furetonide, triamcinolone hexacetonide, betamethasone acetate, dexamethasone, fluorometholone, fluocinolone acetonide, prednisone, prednisolone, methylprednisone, corticol, cortisone, fluorocortisone, deoxycorticosterone acetate, aldosterone and budesonide.

4. The medical article of claim 3, wherein the corticosteroid is selected from the group consisting of triamcinolone, dexamethasone, prednisone and prednisolone.

5. The medical article of claim 4, wherein the corticosteroid is triamcinolone.

6. The medical article of claim 1, wherein:
   (a) the anti-bacterial agent is moxifloxacin; and
   (b) the corticosteroid is triamcinolone or a derivative thereof.

7. The medical article of claim 1, wherein the solubilizing and suspending agent is selected from the group consisting of non-ionic polyoxyethylene-polyoxypropylene block copolymers.

8. The medical article of claim 7, wherein the non-ionic polyoxyethlene-polyoxypropylene block copolymer is poly (ethylene glycol)-block-poly(propylene glycol)-block-poly (ethylene glycol).

9. The medical article of claim 1, wherein in the pharmaceutical composition:
   (a) the anti-bacterial agent is moxifloxacin at a concentration of about 1.0 mg/mL;
   (b) the corticosteroid is triamcinolone acetonide at a concentration of about 15.0 mg/mL; and
   (c) the solubilizing and suspending agent is poly(ethylene glycol)-block-poly(propylene glycol)-block-poly(ethylene glycol) at a concentration of about 1.0 mass %.

10. The medical article of claim 1, wherein the lens is a hydrophilic intraocular lens.

11. The medical article of claim 10, wherein the intraocular lens is fabricated of poly(2-hydroxyethyl methacrylate).

12. A medical article of manufacture, consisting of:
   (a) an intraocular lens that is originally free of pharmaceutically active compounds; and
   (b) a pharmaceutical composition incorporated into the lens, wherein the pharmaceutical composition is a suspension consisting of:
      (b1) a dispersed phase consisting of solid particles consisting of a therapeutically effective quantity of a corticosteroid and pharmaceutically acceptable salts, hydrates, solvates, ethers, esters, acetals and ketals thereof; and
      (b2) a dispersion medium consisting of:
         (1) a therapeutically effective quantity of an anti-bacterial agent independently selected from the group consisting of quinolone, a fluorinated quinolone and pharmaceutically acceptable salts, hydrates, solvates or N-oxides thereof;
         (2) a therapeutically effective quantity of a pharmaceutically acceptable solubilizing and suspending agent selected from the group consisting of non-ionic polyoxyethlene-polyoxypropylene block copolymers and polysorbates;
         (3) a therapeutically effective quantity of a glycopeptide antibiotic selected from the group consisting of vancomycin, teicoplanin, telavancin, decaplanin, ramoplanin, gentamicin, tobramycin, amikacin, cefuroxime, polymyxin B sulfate, and trimethoprim; and
         (4) a pharmaceutically acceptable carrier,
wherein the dispersed phase is dispersed within the dispersion medium, and wherein at least about 99.8% of all the solid particles in the dispersed phase have a size of 10 μM or less.

13. The medical article of claim 12, wherein the anti-bacterial agent is a fluorinated quinolone selected from the group consisting of moxifloxacin and gatifloxacin.

14. The medical article of claim 12, wherein the corticosteroid is selected from the group consisting of triamcinolone, triamcinolone acetonide, triamcinolone diacetate, triamcinolone benetonide, triamcinolone furetonide, triamcinolone hexacetonide, betamethasone acetate, dexamethasone, fluorometholone, fluocinolone acetonide, prednisone, prednisolone, methylprednisone, corticol, cortisone, fluorocortisone, deoxycorticosterone acetate, aldosterone and budesonide.

15. A medical article of manufacture, consisting of:
   (a) an intraocular lens that is originally free of pharmaceutically active compounds; and
   (b) a pharmaceutical composition incorporated into the lens, wherein the pharmaceutical composition is a suspension consisting of:
      (b1) a dispersed phase consisting of solid particles consisting of a therapeutically effective quantity of a corticosteroid and pharmaceutically acceptable salts, hydrates, solvates, ethers, esters, acetals and ketals thereof; and
      (b2) a dispersion medium consisting of:
         (1) a therapeutically effective quantity of an anti-bacterial agent independently selected from the group consisting of quinolone, a fluorinated quinolone and pharmaceutically acceptable salts, hydrates, solvates or N-oxides thereof;
         (2) a therapeutically effective quantity of a pharmaceutically acceptable solubilizing and suspending agent selected from the group consisting of non-ionic polyoxyethlene-polyoxypropylene block copolymers and polysorbates;
         (3) a therapeutically effective quantity of a non-steroid anti-inflammatory drug selected from the group consisting of bromfenac, ketorolac, etodolac, sulindac, diclofenac, aceclofenac, nepafenac, tolmetin, indomethacin, nabumetone, ketoprofen, dexketoprofen, ibuprofen, flurbiprofen, dexibuprofen, fenoprofen, loxoprofen, oxaprozin, naproxen, aspirin, salicylic acid, diflunisal, salsalate, mefenamic acid, meclofenamic acid, flufenamic acid, tolfenamic acid, meloxicam, piroxicam, ternoxicam, droxicam, lornoxicam, isoxicam, celecoxib, rofecoxib, valdecoxib, parecoxib, lumiracoxib, etoricoxib, firocoxib, nimesulide, clonixin, licofelone, and pharmaceutically acceptable salts, hydrates, solvates, ethers, esters, acetals and ketals thereof; and
         (4) a pharmaceutically acceptable carrier,
wherein the dispersed phase is dispersed within the dispersion medium, and wherein at least about 99.8% of all the solid particles in the dispersed phase have a size of 10 μM or less.

16. The medical article of claim 15, wherein the anti-bacterial agent is a fluorinated quinolone selected from the group consisting of moxifloxacin and gatifloxacin.

17. The medical article of claim 15, wherein the corticosteroid is selected from the group consisting of triamcinolone, triamcinolone acetonide, triamcinolone diacetate, triamcinolone benetonide, triamcinolone furetonide, triamcinolone hexacetonide, betamethasone acetate, dexamethasone, fluorometholone, fluocinolone acetonide, prednisone, prednisolone, methylprednisone, corticol, cortisone, fluorocortisone, deoxycorticosterone acetate, aldosterone and budesonide.

* * * * *